Figure 1:
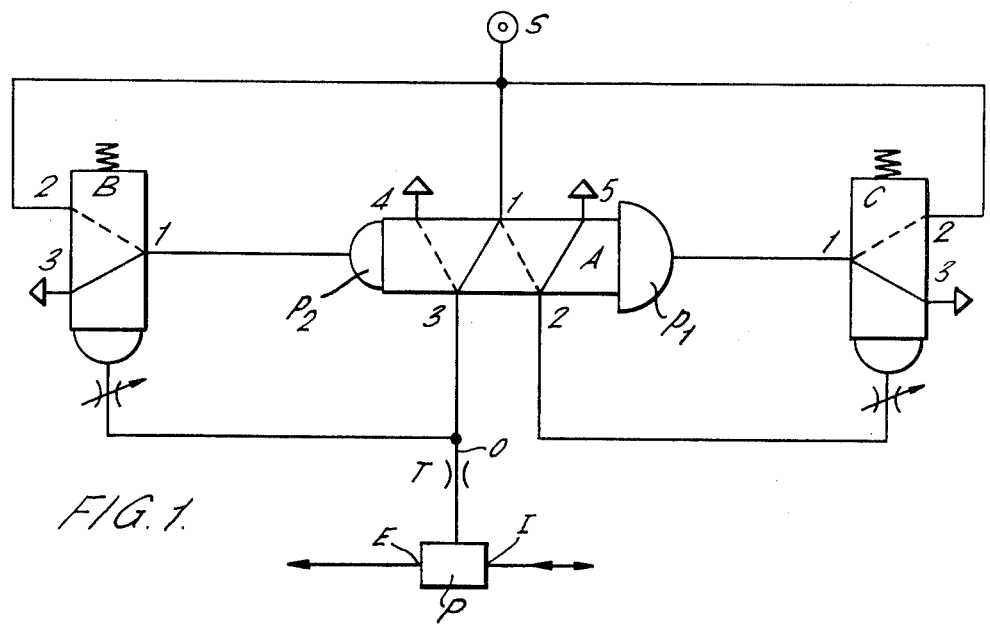

United States Patent [19]

Jones

[11] 4,033,343

[45] July 5, 1977

[54] LUNG VENTILATION EQUIPMENT

[75] Inventor: Norman Stewart Jones, Leighton Buzzard, England

[73] Assignee: Pneupac Limited, London, England

[22] Filed: Nov. 18, 1975

[21] Appl. No.: 632,963

[30] Foreign Application Priority Data

Nov. 26, 1974 United Kingdom ............ 51251/74

[52] U.S. Cl. .......................................... 128/145.8
[51] Int. Cl.² ..................................... A61M 16/00
[58] Field of Search ............ 128/145.8, 145.5, 188; 137/88

[56] References Cited

UNITED STATES PATENTS

| | | | |
|---|---|---|---|
| 3,683,951 | 8/1972 | Beaumint | 128/145.8 |
| 3,809,109 | 5/1974 | Breiling et al. | 137/88 |
| 3,889,669 | 6/1975 | Weigh | 128/145.8 |
| 3,915,164 | 10/1975 | Bird | 128/145.8 |

Primary Examiner—Robert W. Michell
Assistant Examiner—Henry J. Recla
Attorney, Agent, or Firm—Kurt Kelman

[57] ABSTRACT

Lung ventilation equipment comprising a gas pulse source delivering pulses of breathable gas to a patient valve for introduction into the respiratory system of a patient for resuscitation or anaesthetic purposes is characterized by a restrictor in the pulse delivery line from the pulse source to the patient valve, the restrictor being constructed to operate in a sonic-flow "choked" condition during passage of a gas pulse therethrough so that system pressures and resistances downstream of the restrictor cannot affect operation of the pulse source. Downstream of such a restrictor, therefore, conduits may be of small bore while the patient valve may be of the low-pressure type that normally requires a large-bore supply conduit.

7 Claims, 2 Drawing Figures

LUNG VENTILATION EQUIPMENT

FIELD OF THE INVENTION

This invention concerns lung ventilation equipment such as used for administration of anaesthetics and/or for resuscitation by assisting or inducing respiration. Whilst adaptable to the administration of anaesthetic gases the present invention is more particularly concerned with resuscitation equipment intended for emergency use for assisting or inducing respiration by direct ventilation of the lungs with a breathable gas such as oxygen.

BACKGROUND TO THE INVENTION

Lung ventilation equipment of the kind with which the invention is concerned comprises means, often an oscillator powered by the breathable gas from a suitable high pressure source, adapted to deliver breathable gas pulses of appropriate volume and at an appropriate repetition rate to a valve associated with a face mask or intratracheal tube: this valve is usually termed "the patient valve" and has the function of switching a connection to the patient's respiratory passages — i.e. a connection to the mask or intratracheal tube, as the case may be — alternatively to an inhalation port connected to the gas pulse source or oscillator, and to an exhalation port. These patient valves are of various designs and have the primary function of responding to the arrival of a breathable gas pulse from the gas pulse source by directing the breathable gas to the patient's respiratory passages and then changing over so as to permit the patient to exhale via the exhalation port. Often these valves are arranged to permit spontaneous breathing by the patient to occur without constraint.

Most patient valves may be broadly classified in one of two groups depending upon the characteristics of the gas pulses delivered by the gas pulse source or oscillator with which they are to be used. Thus there are the so-called "low-pressure" patient valves, mainly intended to be connected to the gas pulse source through large bore connections and to handle relatively large tidal volumes of gas delivered at relatively low pressures by the pulse source. There are, on the other hand, so-called "high-pressure" patient valves adapted for use with pulse sources that deliver pulses of breathable gas at relatively high pressure, the gas being expanded in passing the patient valve so as to be delivered at the appropriate pressure to the patient's respiratory passages. Because of the higher pressures available to overcome flow path resistance and the smaller volumes of gas, at the higher pressures, to be transmitted from the pulse source to a high-pressure patient valve, relatively small bore tubing can be used between the pulse source and the patient valve and the operation of such a patient valve is inherently more reliable owing to the larger forces available from the high pressure gas to accomplish movement of its moving parts.

In the case of constant-flow equipment having a low-pressure pulse source and a low-pressure patient valve the large bore connections needed between the pulse source and patient valve to handle the required tidal flow volumes with minimum pressure drop and flow restriction increase the pneumatic compliance of the system downstream of the pulse source and prevent the generation, at the patient, of the ideal pressure waveforms for effective lung ventilation.

In the case of constant-flow equipment having a high-pressure pulse source and high-pressure patient valve connected by relatively small bore tubing there is obtained the advantages of compactness and reduced pneumatic compliance downstream of the pulse source. However, it has hitherto been accepted that the length and other physical characteristics of the small bore tubing must affect the gas flow rate and that the latter will also be influenced by manufacturing tolerances in the patient valve; for this reason such equipment is always calibrated and adjusted as a complete system including the patient valve and connecting tubing that are selected to be used with the pulse source of the equipment.

An object of the present invention is to provide a lung ventilating equipment that has the above-discussed advantages of equipment using small bore connections but avoids the disadvantages usually associated therewith.

SUMMARY OF THE INVENTION

In accordance with the present invention, lung ventilation equipment comprising a gas pulse source delivering pulses of breathable gas to a patient valve is characterised by a sonic-flow restrictor in the line from the pulse source to the patient valve, the arrangement being such that during each breathable gas pulse delivered by the pulse source, flow through said restrictor attains sonic velocity and is thus independent of changes in downstream pressure.

The invention is applicable to equipment with either a low-pressure or a high-pressure pulse source and with either a low-pressure patient valve or a high-pressure patient valve.

The restrictor is preferably disposed adjacent to the gas pulse source and arranged to produce pulses appropriate to the type of patient valve in use and although the invention is advantageously embodied in equipment having a high-pressure patient valve in order that certain of the advantages that flow from the use of such a valve may be realised, an important advantage of the invention is that, since pneumatic resistance downstream of the restrictor cannot affect the delivery of the gas pulse source, a low-pressure patient valve can be used and, in contradistinction to normal practice, fed through small-bore tubing to provide at the patient valve pressure waveforms that give rise to most efficient lung ventilation.

Ideally, however, the invention is embodied in lung ventilation equipment having a patient valve of the construction described in my copending U.S. Pat. application Ser. No. 574097, filed May 2, 1975, that realises certain of the operating advantages of a high-pressure valve in response to pulses of relatively low-pressure — e.g. 0.15 bar or less.

It can be shown that the attainment of sonic flow velocity in a restrictor by a compressible gas depends upon the attainment of an appropriate minimum pressure ratio across the restrictor, this minimum pressure ratio being given by the equation:

$$2P1 = (\gamma - 1) P2 (\gamma - 1/\gamma)$$

In this equation, $P1$ is the absolute pressure upstream of the restrictor; $P2$ is the absolute pressure downstream of the restrictor; and $\gamma$ is the ratio of the specific heats of the gas at constant volume and constant pressure, respectively. For diatomic gases, such as oxygen and other components of air, $\gamma$ is approximately 1.4; accordingly for such gases, sonic flow velocity and "choking" of a restrictor will be achieved when the pressure ratio P1/P2 is 1.89.

Thus it should be understood that, by so arranging the system that the pressure ratio (P1/P2) across the sonic flow restrictor is substantially greater than that required for sonic flow with the downstream pressure (P2) at its highest anticipated level in normal operation of the equipment, sonic flow will result in the restrictor over a wide range of operating conditions, and the restrictor will efectively isolate the gas pulse source from all effects of changes in the flow resistance downstream of the restrictor. By the use of small-bore tubing downstream of the restrictor, pressure waves of the required waveform may readily be generated at the patient's lungs and be unaffected by changes in lung compliance.

An additional advantage of the arrangement in accordance with the invention is that variations in the flow resistance of the patient valve, of whatever type, do not affect the delivery of the gas pulse source, with the result that patient valves having a wider range of manufacturing tolerances may be connected via the sonic-flow restrictor to gas pulse sources such as gas-powered oscillators having fixed delivery characteristics and without risk of alteration of those characteristics.

Preferably the invention is applied to lung ventilation equipment having a breathable gas-powered oscillator constructed as described in the copending U.S. Pat. application Ser. No. 632,962, of Normal S. Jones and Geoffrey R. Bennett, filed concurrently herewith.

THE DRAWINGS AND DESCRIPTION OF PREFERRED EMBODIMENT

Figure 2:
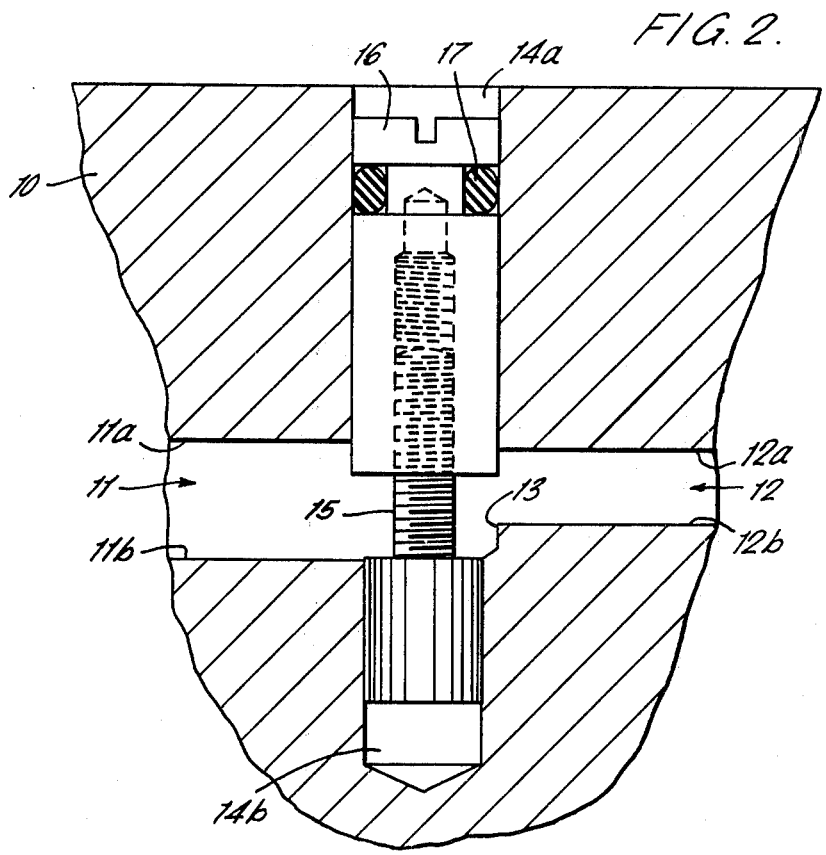

The invention will be further explained with reference to the accompanying drawings, in which:

FIG. 1 is a schematic diagram of lung ventilation equipment embodying the invention; and FIG. 2 is a fragmentary sectional view of a sonic-flow restrictor that may be used in constructing lung ventilation equipment in accordance with the invention.

In FIG. 1, components are shown, where appropriate, by conventional symbols. The lung ventilation equipment shown in this Figure incorporates an oscillator constructed in accordance with the teachings of the aforesaid copending application of Jones and Bennett and comprising an asymmetrically-piloted five-port valve A with associated timer valves B and C.

The five-port valve A is shown symbolically as being asymmetrically piloted by having one pilot, $p_1$, of larger effective area than its other pilot, $p_2$, although in construction the pilots $p_1$, $p_2$ may have equal effective areas with spring or like biasing assisting the pilot $p_1$.

The valve A is of open-center supply configuration, having a center supply port 1 that is connected to both of its outlet ports 2, 3 when the spool of the valve is in its mid-stroke position; however it is of closed-center exhaust configuration, neither of its exhaust ports 4, 5 being connected to any other port of the valve in the mid-stroke position. As symbolically indicated, the application of pilot pressure to pilot $p_1$ shifts the spool of the valve to the stroke end position in which the broken line inter-port connections are set up, viz supply port 1 to outlet port 2 and outlet port 3 is exhaust port 4, while application of pilot pressure to pilot $p_2$ sets up the full-line inter-port connections of supply port 1 to outlet port 3 and outlet port 2 to exhaust port 5. Because the pilots $p_1$, $p_2$ are asymmetric as above explained, application of pilot pressure to both pilots will cause the valve to set up the (broken line) connections normally obtained by the application of pilot pressure to the pilot $p_1$ alone.

The timer valves B, C are of the common construction, being three-port valves with spring-biased spools that have a quiescent position in which the full-line connections, port 1 to port 2, are set up. The valves B and C have pilots fed through adjustable restrictors so that the build-up of sufficient thrust to overpower the spring-biasing of the spool, to set up the broken line, port 1 to port 3, connections, occurs after an interval from the application of pressure to the associated restrictor.

In the oscillator circuit shown, the port 2 of each timer valve is connected to a pressure source that is conveniently the source S for the port 1 of the valve A and may, for instance, be a source of compressed breathable gas such as air or oxygen or an anaesthetic gas, mixture in the case of application of the oscillator to lung-ventilating equipment. The port 3 of each timer valve is connected to exhaust while the ports 1 of the valves B and C are respectively connected to the pilots $p_2$, $p_1$ of the valve A.

Outlet port 2 of the valve A is connected to the pilot of the timer valve C while the outlet port 3 of valve A is connected both to the pilot of timer valve B and to a pulse output line O.

From the foregoing description it will be apparent that, in the absence of source pressure at S, the timer valves B and C will (usually) adopt their quiescent position, connecting both pilots $p_1$, $p_2$ of the valve A to exhaust. If it is assumed that the valve A has stopped with its spool in any position other than mid-stroke, the application of pressure at S will result in pressure fluid passing via one or other of the outlet ports 2, 3 of valve A (depending on the spool position) to the pilot of the associated timer valve C or B: after an interval determined by the setting of the restrictor thereof, the timer valve in question will "fire" to apply source pressure through its port 1 to the pilot $p_1$ or $p_2$ of the valve A, as the case may be, the arrangement being such that this will result in movement of the spool of valve A to its opposite stroke end position, changing over the connection of the source to the port 3 or 2 that previously was connected (via port 4 or 5) to exhaust, and conversely. The fired timer valve will then revert to its quiescent position while the previously quiescent timer valve will fire after an interval determined by the setting of its restrictor, to apply pressure to the other pilots, $p_2$ or $p_1$, of the valve A and cause this to change over again.

Accordingly, for so long as source pressure is applied at S, the valve A will change over at intervals determined by the settings of the restrictors of the timer valves B and C.

In the arrangement shown, whenever the valve A is in the condition resulting from the firing of timer valve B and the application of pressure to pilot $p_2$ of valve A, source S will be connected to the pulse outlet line O. This line extends, in accordance with the invention, through a sonic-flow restrictor in the form of a throttle T to a patient valve P that is preferably of the construction disclosed in the copending U.S. Pat. application Ser. No. 574097, filed May 2, 1975, and having an inhalation port I for connection to the respiratory system of a patient, as by an oronasal mask of intratracheal tube, and an exhalation port E. Downstream of the throttle T, the line O is preferably of small-bore flexible tubing and the throttle T is preferably arranged in the line O close to the port 3 of the valve A but downstream of the connection to the restrictor of timer valve B.

The throttle T is so constructed and adjusted as to operate under a "choked" sonic-flow condition with a pressure ratio of at least 1.9 and preferably at least 2.0 for all anticipated pressures in the line O downstream of the throttle T in normal operation of the equipment.

The construction of a suitable form of throttle T is illustrated in FIG. 2. As shown in this Figure, the throttle comprises a body 10 only part of which is shown and that may be a part of a manifold or connector block providing suitably interconnected ports adapted for connection respectively to the port 3 of valve A, the restrictor of timer valve B, and to a tube constituting the downstream part of the line O.

The body 10 is formed with an inlet passage 11 of circular cross-section and an aligned but not coaxial outlet passage 12, also of circular cross section and with its axis offset from the axis of passage 11 by the difference in the radii of the two passages so that both passages have colinear wall portions 11a, 12a and non-aligned opposite wall portions 11b, 12b joining in a sharp-edged step 13.

The passage 11 is intersected by a bore having a larger diameter portion 13a extending radially outwardly from the colinear wall portions 11a, 12a of the passages 11, 12 and a smaller diameter portion 14b adjacent to but slightly upstream of the step 13. The bore 14b receives the head of a setscrew 15 that extends diametrally across the passage 11 and axially within the bore portion 14a. The head of the setscrew 15 is ribbed and is a forcefit in the bore portion 14b; that surface of the head facing the passage 11 is shaped to match the curvature of the wall portion 11b and thus forms a continuation of that wall portion.

The bore portion 14a is fitted with an adjustable plug 16 that has a screwthreaded bore engaging the setscrew 15 and a kerf accessible from the external end of the bore portion 14a whereby the plug 16 may be rotated by a tool such as a screwdriver to adjust its position along the setscrew 15. The plug 16 is a running fit in the bore portion 14a and has a peripheral groove fitted with a sealing ring 17 to prevent leakage between the plug and the wall of the bore 14a.

As illustrated, the plug 16 is set to project into the passage 11 to an extent sufficient to restrict the entry to the passage 12 to generate the required pressure drop, and upstream/downstream pressure ratio, when gas flows through the throttle and the line O at the required rate.

I claim:

1. Lung ventilation equipment comprising: an upstream gas pulse source adapted to deliver pulses of breathable gas under pressure at an operating flow rate; downstream patient valve; a line connecting the gas pulse source to the patient valve for delivering the gas pulses from the source to the patient valve; and a sonic-flow restrictor in the line, the restrictor being adjustable for control of the flow rate and having means causing a pressure drop during each breathable gas pulse delivered by the pulse source through the line to the patient valve, the means being arranged to cause the pressure drop predominantly due to choking as a result of sonic flow velocity and negligibly due to resistive impedance, the flow thus being independent of changes in the downstream pressure.

2. The equipment of claim 1 in which said restrictor is disposed adjacent to said gas pulse source.

3. The equipment of claim 2 in which said patient valve is of the low-pressure type and is connected to said restrictor by small-bore tubing.

4. The equipment of claim 1 in which said restrictor means provides an upstream/downstream pressure ratio of at least about 1.9 for all normal operating pressures downstream of said restrictor.

5. The equipment of claim 1 wherein the means causing a pressure drop includes a restrictor orifice of constant area and negligible width, and further comprising means adjacent the orifice for varying the area whereby the restrictor is adjustable.

6. The equipment of claim 5, wherein the restrictor orifice is defined between two passages of different diameters, a step being formed between the passages at the orifice, and the area varying means comprises a member adjustably movable across the larger diameter passage adjacent the step.

7. The equipment of claim 6, wherein the step defines a sharp edge between the passages.

* * * * *